(12) United States Patent
Lloyd et al.

(10) Patent No.: US 10,504,619 B2
(45) Date of Patent: *Dec. 10, 2019

(54) SYSTEMS AND METHODS FOR TRANSLATING MESSAGES BETWEEN A HEALTHCARE ENTITY AND A VENDOR ENTITY

(71) Applicant: Redox, Inc., Madison, WI (US)

(72) Inventors: James Lloyd, Madison, WI (US); Christopher Tobin-Campbell, Madison, WI (US); Andrew Kitson, Madison, WI (US); Nicholas Hatt, Madison, WI (US); Nijay Patel, Madison, WI (US)

(73) Assignee: Redox, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/360,493

(22) Filed: Mar. 21, 2019

(65) Prior Publication Data

US 2019/0221296 A1 Jul. 18, 2019

Related U.S. Application Data

(63) Continuation of application No. 15/965,084, filed on Apr. 27, 2018, now Pat. No. 10,242,755, which is a
(Continued)

(51) Int. Cl.
*G16H 10/60* (2018.01)
*G06F 16/33* (2019.01)
(Continued)

(52) U.S. Cl.
CPC ............ *G16H 10/60* (2018.01); *G06F 16/258* (2019.01); *G06F 16/33* (2019.01); *G16H 40/20* (2018.01); *H04L 51/08* (2013.01); *H04L 67/12* (2013.01)

(58) Field of Classification Search
CPC .. G16H 10/60; G16H 40/20; G06F 17/30569; G06F 19/30634; G06F 16/33; G06F 16/258; H04L 51/08; H04L 67/12
(Continued)

(56) References Cited

U.S. PATENT DOCUMENTS 7,752,035 B2 7/2010 Oon
8,000,984 B2 8/2011 Hasan
(Continued)

*Primary Examiner* — Joy Chng
(74) *Attorney, Agent, or Firm* — Esplin & Associates, PC

(57) ABSTRACT

An inbound message including medical record content may be received. The inbound message may indicate a healthcare entity and a vendor entity. It may be determined, from the healthcare entity and stored correspondences between medical record formats and healthcare entities, that the medical record content of the inbound message is in a first medical record format. Which configuration record of stored configuration records specifying combinations of sets of rules may be determined to apply as a translation to the inbound message based upon the medical record content of the inbound message and the first medical record format. The sets of rules as indicated by the configuration record may be accessed and applied to the inbound message to translate the medical record content in the inbound message from the first medical record format to the standardized format. The standardized format may be transmitted to the vendor entity.

20 Claims, 5 Drawing Sheets

Related U.S. Application Data continuation of application No. 15/289,017, filed on Oct. 7, 2016, now Pat. No. 9,996,664.

(51) Int. Cl.
*G06F 16/25* (2019.01)
*G16H 40/20* (2018.01)
*H04L 12/58* (2006.01)
*H04L 29/08* (2006.01)

(58) Field of Classification Search
USPC .......................................................... 705/2–3
See application file for complete search history.

(56) References Cited

U.S. PATENT DOCUMENTS

| | | |
|---|---|---|
| 8,260,635 B2 | 9/2012 | Hasan |
| 8,850,057 B2 | 9/2014 | Natoli |
| 2001/0053986 A1 | 12/2001 | Dick |
| 2004/0068545 A1 | 4/2004 | Daniell |
| 2005/0138210 A1 | 6/2005 | Shkvarchuk |
| 2007/0016450 A1* | 1/2007 | Bhora ................... G16H 10/60 705/3 |
| 2008/0046292 A1 | 2/2008 | Myers |
| 2009/0222283 A1 | 9/2009 | Lassetter |
| 2011/0106564 A1 | 5/2011 | Hachmeister |
| 2015/0332011 A1 | 11/2015 | Ting |
| 2016/0063191 A1* | 3/2016 | Vesto ................... G06F 19/324 705/2 |

* cited by examiner

SYSTEMS AND METHODS FOR TRANSLATING MESSAGES BETWEEN A HEALTHCARE ENTITY AND A VENDOR ENTITY

FIELD

The disclosure relates to systems and methods for translating messages that include medical record content between a healthcare entity and a vendor entity based upon a health record format associated with the healthcare entity.

BACKGROUND

Medical records are an important aspect of medical treatment for a patient. Medical records include a variety of information regarding the patient's biographical and/or demographical information. Paper-based medical records have moved to electronic medical records. Electronic medical records may be stored in various formats, some of which have been attempted to be standardized. Interaction between healthcare providers and service providers have been increasingly difficult with differences in communications including content formatted in different ways.

SUMMARY

The disclosure relates to translating messages that include medical record content between a healthcare entity and a vendor entity, in accordance with one or more implementations. Data from healthcare entities (e.g., healthcare providers) may be represented in a variety of formats (e.g., medical record formats). Within individual formats, representation of information (e.g., patient identifiers, patient name, patient sex, etc.) inside messages may vary across electronic health records and healthcare systems. Messages may be translated such that messages may be received and/or transmitted in any format or structure (e.g., medical record format) associated with the healthcare entity. A translation may be applied to the messages to translate and/or normalize the medical record content included within the messages to a standardized format. The medical record format and/or the medical record content may be standardized such that similar information (e.g., patient ID, patient sex, etc.) may be found in the same place within the standardized format regardless of the source of the information (e.g., regardless of the healthcare entity and/or the vendor entity). The translation may be applied and/or performed bi-directionally, such that outgoing messages from healthcare entities and/or incoming messages to healthcare entities may be translated to and/or from the standardized model based upon the medical record format associated with the receiving and/or transmitting healthcare entity.

In some implementations, a system configured to translate messages that include medical record content between a healthcare entity and a vendor entity may include one or more servers. The server(s) may be configured to communicate with one or more client computing platforms according to a client/server architecture. The server(s) may be configured to execute one or more computer program components. The computer program components may include one or more of an receiving component, a determination component, a translation component, a transmission component, and/or other components.

The system may provide a consistent experience to consumers of healthcare entities and/or vendor entities. Messages may be translated to a standardized format and the standardized format may be exposed via an application program interface. Applications associated with the vendor entities may interact with the standardized format, making communications and/or integration with healthcare entities with varying medical record formats easy and seamless. Vendor entities and/or healthcare entities may connect quickly without having to customize their own systems for individual medical record formats in order to communicate with different entities associated with different medical record formats.

Electronic storage may be configured to store correspondences between medical record formats and healthcare entities, including a correspondence between a first medical record format and a first healthcare entity and a correspondence between a second medical record format and a second healthcare entity. The correspondences may include past and/or current correspondences between medical record formats and healthcare entities. The correspondences may be used to determine medical record formats of messages being transmitted between healthcare entities and/or vendor entities. Healthcare entities may include healthcare providers, such as medical offices, hospitals, medical labs, public healthcare agencies, and the like. The healthcare entities may store medical record information.

Medical record information may be stored by healthcare entities in the form of electronic health records. An electronic health record may include a digital version of traditional paper-based medical records. An electronic health record may be stored in different formats (e.g., medical record formats) for different healthcare entities. Medical record formats may include Health Level 7 (HL7), XML, JSON, Edifact, Dicom, X12N, NCPDP, and/or other medical record formats. The medical record formats may include any past medical record formats, current medical record formats, and/or future medical formats.

Electronic storage may be configured to store sets of rules. The sets of rules may be used in different combinations to translate messages between multiple medical record formats and a standardized format. The multiple medical record formats may include the first medical record format and the second medical record format.

Electronic storage may be configured to store configuration records. The configuration records may specify combinations of the stored sets of rules to translate messages between multiple medical record formats and the standardized format. The configuration records may include a first configuration record for the first medical record format and a second configuration record for the second medical record format.

The receiving component may be configured to receive an inbound message including medical record content. The inbound message may indicate the healthcare entity and a vendor entity. The inbound message may include any of the medical record information (e.g., medical record content) discussed above. The inbound message may indicate the healthcare entity (e.g., the inbound message may indicate that the inbound message originated from healthcare entity A). The inbound message may indicate the vendor entity for which the inbound message may be transmitted to (e.g., the vendor entity may include the destination of the inbound message). The vendor entity may include applications associated with a service provider for the healthcare entity. For example, the vendor entity may include an insurance company, a pharmacy, and/or other service providers that may communicate and/or interact with healthcare entities and/or providers.

The determination component may be configured to determine, from the stored correspondences and indication of the healthcare entity in the inbound message, that the medical record content of the inbound message is in the first medical record format. As discussed above, medical record content originating from different healthcare entities may vary in format, style, and/or content. Based upon previously stored correspondences and the indication of indication of healthcare entity 200a, the determination component may be configured to determine in or near real-time that the first medical record format of the inbound message may be HL7.

Based on the determination that the medical record content of the inbound message is in the first medical record format, the translation component may be configured to apply a translation to the inbound message that translates the medical record content in the inbound message from the first medical record format to a standardized format.

The stored configuration records may start at a generalized level. One or more configuration records may be more specific as needed based upon customizations and workflows of the various applications and/or medical record formats associated with the healthcare entities and/or vendor entities. The system may be configured to re-utilize and/or combine existing configuration records via a nesting logic for various translations. As such, one or more configuration records may specify sets of rules that reference nested configuration records. The nested configuration records may specify combinations of sets of rules that are common between the one or more configuration records that reference the nested configuration records. For example, if three different configuration records reference the same nested configuration record, the same sets of rules specified by the nested configuration records may be applied by all three configuration records.

The translation component may be configured to determine which configuration record to apply as a translation to the inbound message based upon the medical record content of the inbound message and the first medical record format. The translation component may be configured to access and apply the sets of rules as indicated by the configuration record to the inbound message to translate the medical record content in the inbound message from the first medical record format to the standardized format. The sets of rules may be access from electronic storage. The sets of rules of the configuration record may be applied in order. The sets of rules of the configuration record may be applied in an order defined by the configuration record. If a nested configuration record is referenced by the configuration record, translation component 110 may be configured to access the nested configuration record and apply the sets of rules as indicated by the nested configuration record when referenced by the configuration record The transmission component may be configured to effectuate transmission of the standardized format to the vendor entity and/or an application associated with the vendor entity indicated within the inbound message. The transmission component may be configured to apply a filter that determines whether to continue transmitting the standardized format to the vendor entity and/or an application associated with the vendor entity. For example, some healthcare and/or vendor entities may only want messages from particular departments to be sent out. Filters may alter the content of the messages, such that only required information may be transmitted (e.g., only required information for a scheduling application, and/or other required information associated with other applications). The standardized format may be consumed by the vendor entity indicated by the inbound message and/or an application associated with the vendor entity indicated by the inbound message via an application program interface associated with the system. The filters may be provided by the individual healthcare entities and/or the individual vendor entities. The filters may be configured, added, deleted, customized, and/or modified by users of the individual healthcare entities and/or the individual vendor entities.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
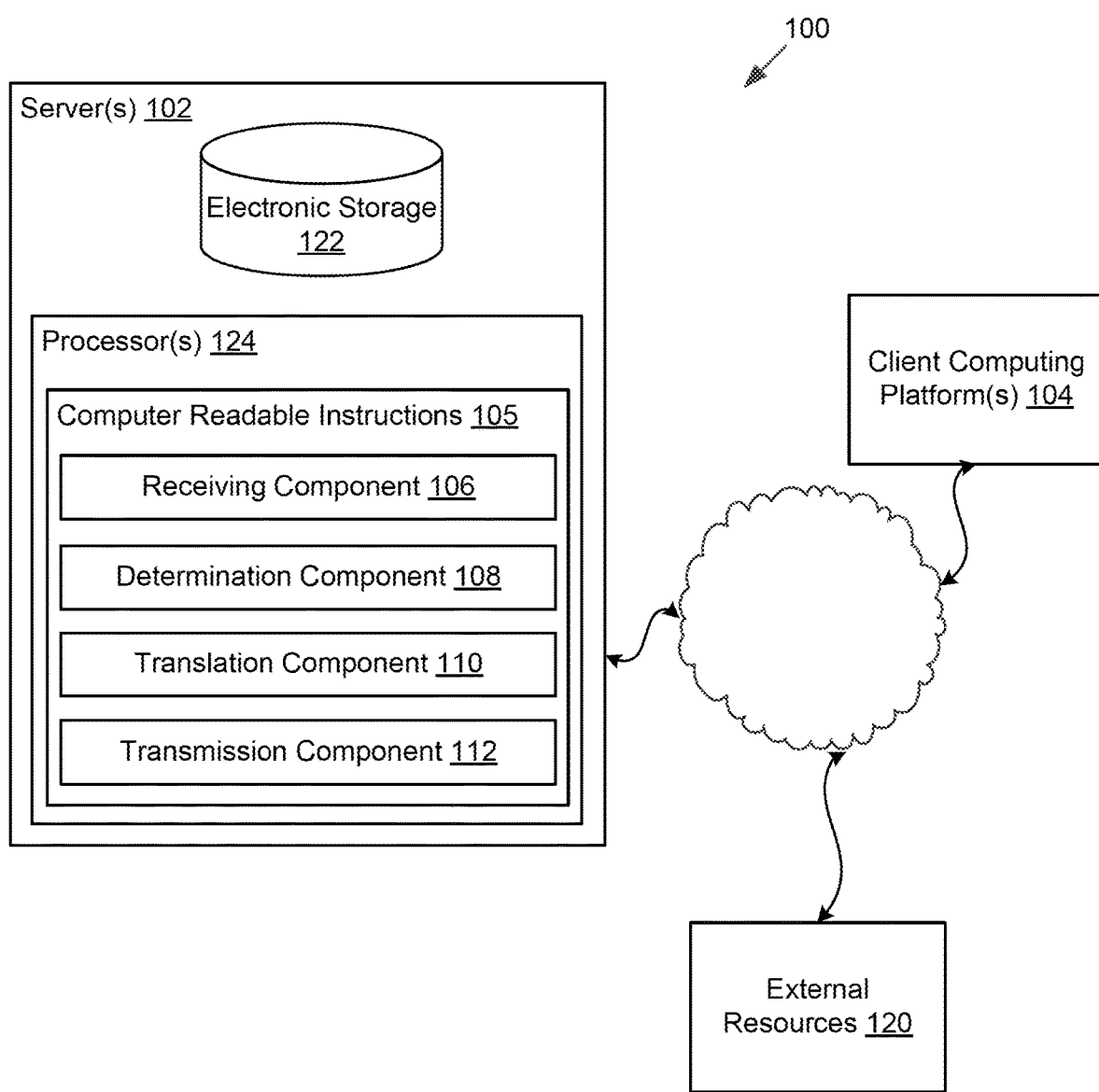
FIG. 1 illustrates a system for translating messages that include medical record content between a healthcare entity and a vendor entity, in accordance with one or more implementations.

FIG. 1 illustrates a system 100 for translating messages that include medical record content between a healthcare entity and a vendor entity, in accordance with one or more implementations. Data from healthcare entities (e.g., healthcare providers) may be represented in a variety of formats (e.g., medical record formats). Within individual formats, representation of information (e.g., patient identifiers, patient name, patient sex, etc.) within messages may vary across electronic health records and healthcare systems. The disclosed system may translate messages such that the system may receive and/or transmit messages in any format or structure (e.g., medical record format) associated with the healthcare entity. A translation may be applied to the messages to translate and/or normalize the medical record content included within the messages to a standardized format. The disclosed system may standardize the medical record format and/or the medical record content such that similar information (e.g., patient ID, patient sex, etc.) may be found in the same place within the standardized format regardless of the source of the information (e.g., regardless of the healthcare entity and/or the vendor entity). The system may perform the translation bi-directionally, such that outgoing messages from healthcare entities and/or incoming messages to healthcare entities may be translated to and/or from the standardized model based upon the medical record format associated with the receiving and/or transmitting healthcare entity.

The system may provide a consistent experience to consumers of healthcare entities and/or vendor entities. Messages may be translated to a standardized format and the standardized format may be exposed via an application program interface. Applications associated with the vendor entities may interact with the standardized format, making communications and/or integration with healthcare entities with varying medical record formats easy and seamless. Vendor entities and/or healthcare entities may connect quickly without having to customize their own systems for individual medical record formats in order to communicate with different entities associated with different medical record formats.

As is illustrated in FIG. 1, system 100 may include one or more server(s) 102. Server(s) 102 may be configured to communicate with one or more client computing platform(s) 104 according to a client/server architecture. Server(s) 102 may be configured to execute one or more computer program components. The computer program components may include one or more of receiving component 106, determination component 108, translation component 110, transmission component 112, and/or other components.

Users may interact with system 100 via one or more client computing platform(s) 104. Client computing platform(s) 104 may include one or more of a cellular telephone, a smartphone, a digital camera, a laptop, a tablet computer, a desktop computer, a television set-top box, a smart TV, a gaming console, and/or other client computing platforms.

Server(s) 102 may include electronic storage 122. Electronic storage 122 may include electronic storage media that electronically stores information. The electronic storage media of electronic storage 122 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage 122 may include one or more virtual storage resources (e.g., cloud storage, a virtual private network, and/or other virtual storage resources). Electronic storage 122 may store software algorithms, information determined by processor(s) 124, information received from server(s) 102, information received from client computing platform(s) 104, and/or other information that enables server(s) 102 to function as described herein.

Electronic storage 122 may be configured to store correspondences between medical record formats and healthcare entities, including a correspondence between a first medical record format and a first healthcare entity and a correspondence between a second medical record format and a second healthcare entity. The correspondences may include past and/or current correspondences between medical record formats and healthcare entities. The correspondences may be used to determine medical record formats of messages being transmitted between healthcare entities and/or vendor entities.

Healthcare entities may include healthcare providers, such as medical offices, hospitals, medical labs, public healthcare agencies, and the like. The healthcare entities may store medical record information. Medical record information may include patient information, such as demographical and biographical information about the patients of the healthcare providers. For example, for an individual patient, a healthcare entity may store the patient's name, sex, age, weight, height, address, blood type, symptoms, medical history, family history, any past and/or present treatments administered, prescribed medication, prescribed procedures, tests, doctors that have treated and/or are treating the patient, and/or other information associated with the patient.

Medical record information may be stored by healthcare entities in the form of electronic health records. An electronic health record may include a digital version of traditional paper-based medical records. An electronic health record may be stored in different formats (e.g., medical record formats) for different healthcare entities. In other words, individual healthcare entities may be associated with different medical record formats such that individual healthcare entities store and/or transmit medical record information in the format associated with the healthcare entity. Medical record formats may include Health Level 7 (HL7), XML, JSON, Edifact, Dicom, X12N, NCPDP, and/or other medical record formats. The medical record formats may include any past medical record formats, current medical record formats, and/or future medical formats. For example, HL7 may include different versions of formats such as HL7v2, HL7v3, and/or other HL7 versions. Individual versions of HL7 formats may be associated with various countries. For example, the medical record format may include an Australian version of HL7v3, a United Kingdom version of HL7v3, a United States version of HL7v3, and/or other versions of HL7. The various medical record formats may refer to a set of international standards and/or framework for the exchange, integration, sharing, and/or retrieval of medical record information between applications (e.g., scheduling applications, billing applications, etc.) used by various healthcare entities and/or vendor entities.

Some medical records formats associated with different healthcare entities may be similar. For example, the first medical record format and the second medical record format may be similar, such that the first medical record format is HL7 and the second medical record format is HL7. The first medical record format and the second medical record format may differ based upon customizations of the individual medical record formats by the individual healthcare entities. For example, the first healthcare entity may customize the first medical record format (e.g., HL7 in this example) based upon needs and/or requirements for the first healthcare entity. Similarly, the second healthcare entity may customize the second medical record format (e.g., HL7 in this example) based upon needs and/or requirements for the second healthcare entity. In this manner, while the first medical record format and the second medical record format are similar in the sense that both are HL7, they are different based upon individual customizations of the first healthcare entity and the second healthcare entity. This is for exemplary purposes only and is not meant to be a limitation of this disclosure.

Medical record information may be represented differently within individual medical record formats. For example, patient sex may be represented differently within different medical record formats. "Female" may be represented as "F", "Female", "FEMALE", "W", "Woman", "WOMAN", as an integer (e.g., 1 or 2) that corresponds to a value for male or female, and/or may be represented in others ways with different medical record formats.

Correspondences between medical record formats and healthcare entities stored within electronic storage 122 may include a correspondence between a first medical record format and a first healthcare entity and a correspondence between a second medical record format and a second healthcare entity. This is for illustrative purposes only, as any number of correspondences between medical record formats and healthcare entities for any number of healthcare entities may be stored within electronic storage 122. Individual healthcare entities may communicate, correspond, and/or interact with applications associated with vendors and/or service providers based upon the medical record format associated with the healthcare entity. For example, a first medical record format for a first healthcare entity (e.g., a hospital) may include HL7. A second medical record format for a second healthcare entity (e.g., a medical office) may include XML.

Electronic storage 122 may be configured to store sets of rules. As will be discussed in further detail below, the sets of rules may be used in different combinations to translate messages between multiple medical record formats and a standardized format. The multiple medical record formats may include the first medical record format and the second medical record format.

Electronic storage 122 may be configured to store configuration records. As will be discussed in further detail below, the configuration records may specify combinations of the stored sets of rules to translate messages between multiple medical record formats and the standardized format. The configuration records may include a first configuration record for the first medical record format and a second configuration record for the second medical record format.

Receiving component 108 may be configured to receive an inbound message including medical record content. The inbound message may indicate the healthcare entity and a vendor entity. The inbound message may include any of the medical record information (e.g., medical record content) discussed above. The inbound message may indicate the healthcare entity (e.g., the inbound message may indicate that the inbound message originated from healthcare entity A). The inbound message may indicate the vendor entity for which the inbound message may be transmitted to (e.g., the vendor entity may include the destination of the inbound message). The vendor entity may include applications associated with a service provider for the healthcare entity. For example, the vendor entity may include an insurance company, a pharmacy, and/or other service providers that may communicate and/or interact with healthcare entities and/or providers.

Figure 2:
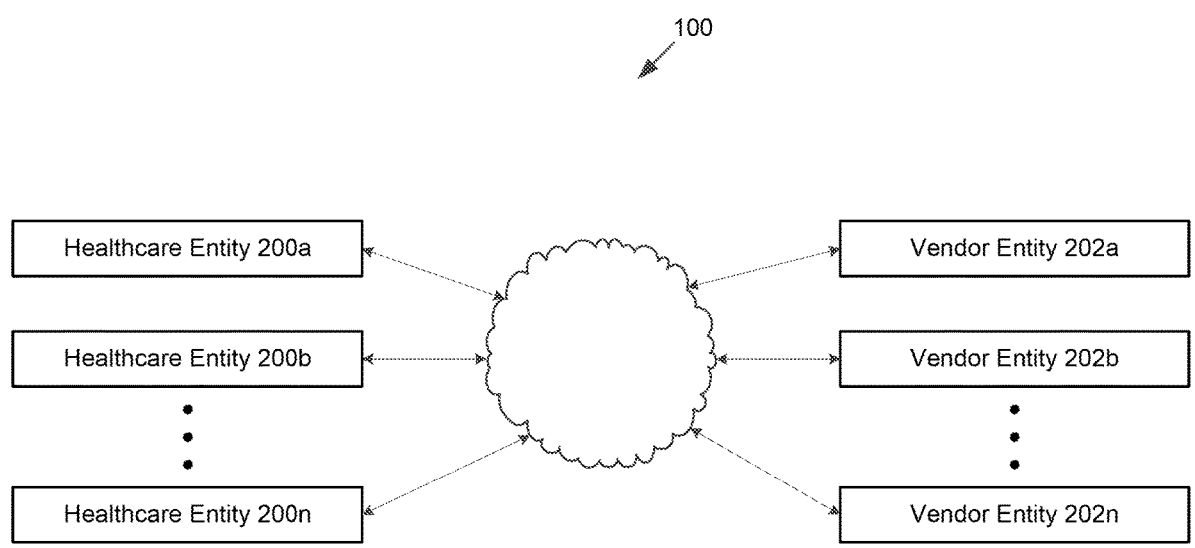
FIG. 2 illustrates a system for translating messages that include medical record content between a healthcare entity and a vendor entity, in accordance with one or more implementations.

Referring to FIGS. 1 and 2, healthcare entities 200a, 200b, ... 200n and vendor entities 202a, 202b, ... 202n are shown. Any number of healthcare entities may be provided. System 100 may not limit the number of healthcare entities system 100 communicates with. Individual healthcare entities may include a combination of various applications used at and/or by the healthcare entity, such as a patient intake tool, a hospital billing program, a scheduling application, and/or other systems and/or applications. Individual healthcare entities may operate in different geographical locations.

Similarly, any number of vendor entities may be provided. System 100 may not limit the number of vendor entities system 100 integrates with. Individual vendor entities may integrate with system 100 such that applications and/or systems used by the individual vendor entities may receive messages and/or transmit messages via an application program interface associated with system 100 in order to receive and/or transmit messages in the standardized format, as will be discussed in further detail below.

The inbound message including medical record content may be received from healthcare entity 200a. The inbound message may indicate that the inbound message originated from healthcare entity 200a. The inbound message may indicate that the destination of the inbound message is vendor entity 202a and/or an application associated with vendor entity 202a. The medical record content may include a large amount of complex data structured differently within the inbound message based upon the medical record format of the inbound message and/or the healthcare entity at which the inbound message originated from. For example, the medical record content may include a patient identification, the patient's name, age, sex, diagnosis, family history, treatment plan, prescription, cost of treatment, and/or other biographical information and/or demographical information associated with the patient, as discussed above.

Determination component 108 may be configured to determine, from the stored correspondences and indication of the healthcare entity in the inbound message, that the medical record content of the inbound message is in the first medical record format. As discussed above, medical record content originating from different healthcare entities may vary in format, style, and/or content. Based upon previously stored correspondences and the indication of indication of healthcare entity 200a, determination component 108 may be configured to determine in or near real-time that the first medical record format of the inbound message may be HL7.

Based on the determination that the medical record content of the inbound message is in the first medical record format (e.g., HL7), translation component 110 may be configured to apply a translation to the inbound message that translates the medical record content in the inbound message from the first medical record format to a standardized format. Applying the translation to the inbound message that translates the medical record content in the inbound message from the first medical record format to the standardized format may include parsing the medical record content in the inbound message into structured objects including data fields. Applying the translation to the inbound message that translates the medical record content in the inbound message from the first medical record format to the standardized format may include translating the structured objects into the standardized format by applying a set of rules that translates the data fields from the structured objects into standardized format fields of the standardized format.

The inbound message may include a particular message structure for individual medical record formats. Given a particular medical record format (e.g., HL7), a specific piece of data (e.g., patient sex, patient identifier, etc.) may reside in different locations within the inbound message. Individual healthcare entities that use the same medical record format may have a specific set of variations in common across their customers. Further, individual healthcare entities may have unique variations within their own customizations from the standard medical record format. As such, simply because HL7 may be associated with and/or used by healthcare entity 200a, it does not necessarily mean that the medical record format of HL7 is the same as the one associated with and/or used by healthcare entity 200n. Individual healthcare entities that utilize HL7 as a health record format may individually customize the health record format for that particular healthcare entity's applications and/or requirements.

Applying the translation to the inbound message that translates the medical record content in the inbound message from the first medical record format to the standardized format may include parsing the medical record content in the inbound message into structured objects including data fields. For example, a structured object may include patient identifiers with data fields including patient ID and a patient ID type.

The inbound message may include string data in the first medical record format (e.g., HL7). For example, the inbound message in the first medical record format (e.g., HL7) may include a patient identifier in the following string: "PID|1||abc123^^^MRN^~9999^^^EMP|^||TEST^JANE||19800101||F|||123". In this example, a patient ID may be included within the inbound message in the patient identification (PID) segment, field 3, component one and an ID type in PID segment, field 3, component four.

A second inbound message in a second medical record format (e.g., XML) may include a patient identifier in the following way:

```
<recordTarget>
  <patientRole>
    <id extension="12345" root="2.16.840.1.113883.19"/>
    ...
  </patientRole>
</recordTarget>
```

A third inbound message in a third medical record format (e.g., JSON) may include a patient identifier in the following string:

{"paitient_id": "acb123"}

Applying the translation to the inbound message that translates the medical record content in the inbound message from the first medical record format to the standardized format may include translating the structured objects into the standardized format by applying a set of rules that translates data fields from the structured objects into standardized format fields. As discussed above, sets of rules may be stored by electronic storage 122. Electronic storage 122 may store configuration records specifying combinations of the sets of rules to apply as the translation to the inbound message. Configuration records may be used to solve the problem that the same variation within medical record formats may be repeated at various different healthcare entities associated with the medical record format. Healthcare entities that utilize the same or similar medical record format may store data that is more alike (e.g., even with customizations to the medical record formats by individual healthcare entities) than healthcare entities that utilize a different medical record format. For individual healthcare entities, configuration records may normalize data for the specific ways that the individual healthcare entities differ from one another that use the same medical record format (e.g., HL7v2, CDA, etc.). Returning to the example of patient sex above, female may be represented differently among different medical record formats. The configuration records may normalize such differences.

Configuration records may specify different combinations of the sets of rules to translate messages between multiple medical record formats and the standardized format. The first configuration record for the first medical record format may specify a first combination of sets of rules to translate the inbound message from the first medical record format to the standardized format. The second configuration record for the second medical record format may specify a second combination of sets of rules to translate the inbound message from the second medical record format to the standardized format. The first combination of the sets of rules associated with the first configuration record and the second combination of the sets of rules associated with the second configuration record may specify the differences between first medical record format and the second medical record based upon the customizations of the individual medical record formats.

Translation component 110 may be configured to determine which configuration record to apply as a translation to the inbound message based upon the medical record content of the inbound message and the first medical record format. For example, if the first medical record format is HL7 and the medical record content of the inbound message includes a patient identifier and a patient address, translation component 110 may be configured to determine which configuration record of the stored configuration records to apply as the translation to the inbound message based upon the first medical record format being HL7 and the medical record content of the inbound message including the patient identifier and the patient address.

The configuration records may use a domain specific language (DSL) to translate the medical record content of the inbound message to the standardized format. Referring to the medical record content included within the inbound message from the example above with HL7 as the first medical record format, a configuration record that may translate the patient identifiers from PID-3 (e.g., PID segment, field 3) may include:

'Patient.Identifiers[PID.3].ID':
  node: 'PID.3.1'
'Patient.Identifiers[PID.3].IDType':
  node: 'PID.3.4.1

The string "'Patient.Identifiers[PID.3].ID'" within the configuration record above may specify a location (e.g., the standardized format field) within the standardized format to store the medical record content. The "node" line may indicate the source (e.g., the data field from the structured object) of the medical record content. The syntax of the "node" line may vary based upon the medical record format of the inbound message. As indicated above, "PID.3.1" may indicate that the patient ID may be pulled from the inbound message (e.g., in the HL7 medical record format) from the PID segment, field 3, component one. This is for exemplary purposes only and is not meant to be a limitation of this disclosure, as multiple sets of rules (e.g., configuration records) may be used to translate the inbound message to and/or from the standardized model.

For an inbound message with an XML medical record format, a configuration record for the XML medical record format may use the xpath query language to specify the source of a given data element within the medical record content. For an inbound message with a JSON medical record format, the same DSL syntax that describes a target location within the standardized format may describe a source location within the medical record content of the inbound message.

The standardized format may include standard "data models" that messages from a healthcare entity and/or application may be normalized to. For example, system 100 may include a "scheduling" data model that may represent how system 100 communicates about patient appointments. The "scheduling data model" may include a standard way of representing the patient, providers, location, time, and/or other aspects of the patient appointment. The standardized format may include arrays to store the normalized and/or translated medical record content. The standardized format may be JSON objects, but this is not meant to be a limitation of this disclosure, as other standardized formats may be contemplated. Continuing with the example above, patient identifiers may be represented in the following standardized format:

```
{
  "Patient": {
    "Identifiers": [{
      "ID": "abc123",
      "IDType": "MRN"
    },{
      "ID": "9999",
      "IDType": "EMPI"
    }]
  }
}
```

In this manner, patient identifiers may be standardized and/or translated to the same standardized format. Further, the translated medical record content of the inbound message may be found in the same location within the standardized format, regardless of the medical record format that the inbound message originated in.

System 100 may be configured to re-use various configuration records that translates the data fields from the structured objects into the standardized format fields. The configuration records may start at a generalized level. The configuration records may then become more specific as needed based upon customizations and workflows of the various applications and/or medical record formats associated with the healthcare entities and/or vendor entities. System 100 may be configured to re-utilize and/or combine existing configuration records via a nesting logic for various translations. As such, one or more configuration records may specify sets of rules that reference nested configuration records. The nested configuration records may specify combinations of sets of rules that are common between the one or more configuration records that reference the nested configuration records. That is, if three different configuration records reference the same nested configuration record, the same sets of rules specified by the nested configuration records may be applied by all three configuration records.

Different configuration records may be applied to translate an inbound message to the standardized format. For example, a first configuration record may include a complete set of mappings that may be customized to translate messages to or from a particular medical record format associated with a source or destination (e.g., individual healthcare entities and/or applications associated with the healthcare entities). The first configuration record may account for any quirks and/or differences within individual medical record formats associated with individual healthcare entities.

Further, a second configuration record may be configured to translate particular data fields. The second configuration record may be incomplete, in that the second configuration record may not completely translate the inbound message on its own. Referring to the example above regarding translating patient identifiers, the second configuration record may map PID-3 to Patient.Identifiers. This may be referred to as a "nested configuration". Nested configurations may include reusable existing sets of rules and/or configuration records that may compose larger sets of rules and/or configuration records to translate messages. Nested configurations may be referred to, referenced, and/or mapped from other configuration records.

Take for example a patient object. The patient object may include a set of address fields. The address fields may be mapped in a configuration record that maps patient address. The patient address may be used to map a provider address and/or a facility address. As such, system 100 may be configured to determine a configuration record that maps addresses and uses the set of rules of that configuration record any time an address may be required. For example, the following configuration records may use the shared configuration records (e.g., id-of-address-config, as shown below) associated with address to populate the patient address and the provider address:

Patient.Address
Node: PID.11
configuration: id-of-address-config
Provider.Address
node: PV1.14
configuration: id-of-address-config
id: id-of-address-config
City:
Node: 3
State:
Node: 4

Nested configurations may encapsulate standard sets of variations between medical record formats. For example, a first medical record format and a second medical record format may handle and/or format patient IDs differently. In this scenario, a configuration record may map the patient object according to the following HL7 specifications:

Patient.Identifiers:
configuration: id-of-standard-config
Patient.Address:
configuration: id-of-standard-address-config
Patient.DOB:
PID.7.1.
. . . .

System 100 may determine two different configuration records for the individual medical record formats. The configuration records may leverage the standard patient mappings and add targeted updates for any quirks in the individual medical record formats associated with the individual healthcare entities. The configuration records may include:

id: ehr-a-config
Patient:
configuration: id-of-standard-patient-config
Patient.Identifiers:
configuration: identifiers-from-pid-2
id: ehr-b-config
Patient:
configuration: id-of-standard-patient-config
Patient.Identifiers[PID.3].IDType:
node: PID.3.5#just override id type, not full id handling
. . . remaining fields For individual healthcare entities associated with a particular medical record format (e.g., the second medical record format), the configuration record may be customized in the following manner:

id: health-system-a
Root:
configuration: ehr-a-config
OBR.20:
node: Order.ID

Translation component 110 may be configured to access and apply the sets of rules as indicated by the configuration record to the inbound message to translate the medical record content in the inbound message from the first medical record format to the standardized format. The sets of rules may be access from electronic storage 122. The sets of rules of the configuration record may be applied in order. The sets of rules of the configuration record may be applied in an order defined by the configuration record. If a nested configuration record is referenced by the configuration record, translation component 110 may be configured to access the nested configuration record and apply the sets of rules as indicated by the nested configuration record when referenced by the configuration record.

Figure 3:
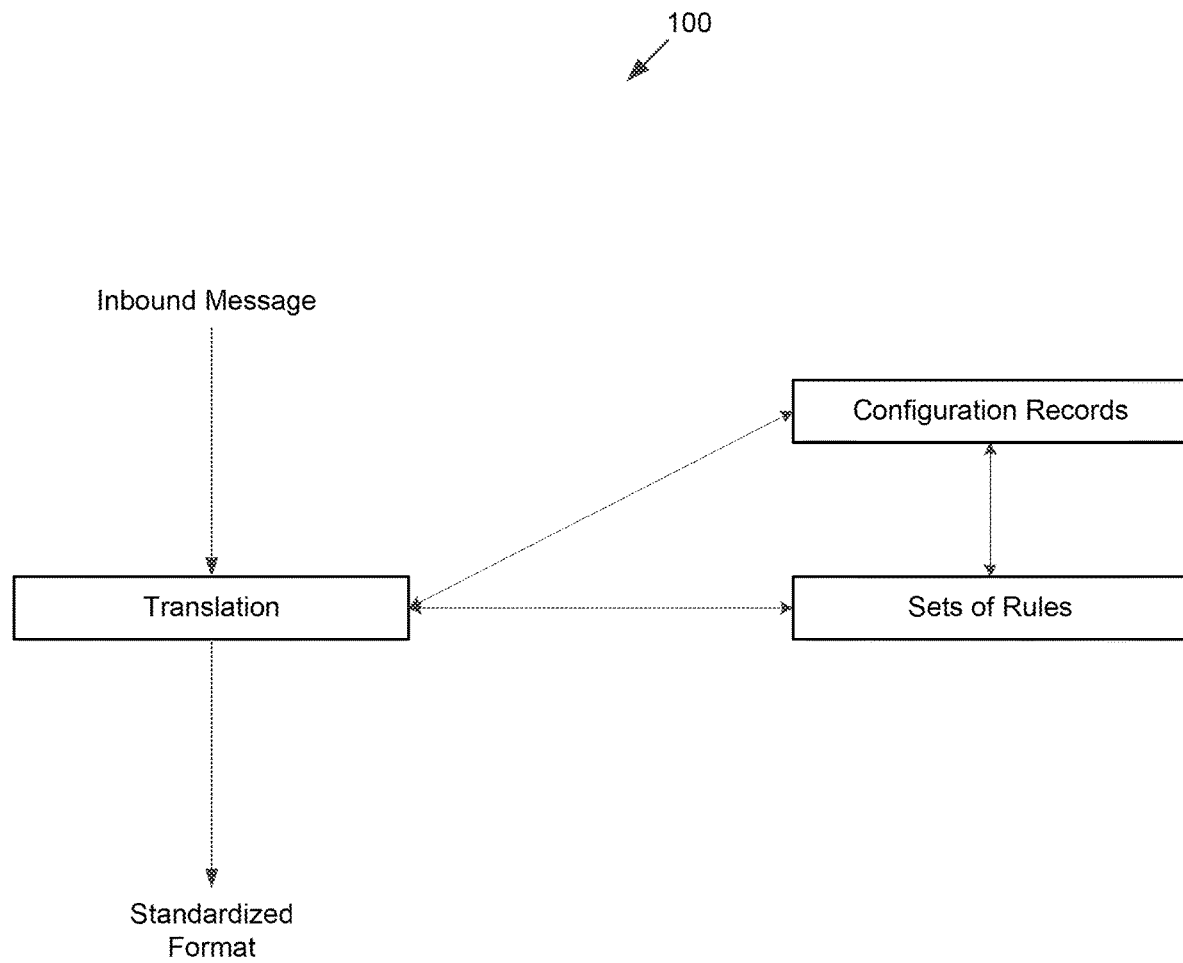
FIG. 3 illustrates a diagram for translating messages that include medical record content between a healthcare entity and a vendor entity, in accordance with one or more implementations.

Referring to FIG. 3, a block diagram of system 100 is provided. As shown in FIG. 3, an inbound message may be received by system 100. As described above, the inbound message may include medical record content. The inbound message may indicate a healthcare entity and a vendor entity. System 100 may be configured to determine, from stored correspondences and the indication of the healthcare entity in the inbound message, the medical record content of the inbound message is in a first medical record format. System 100 may be configured to apply a translation to the inbound message. The translation may be based upon stored configuration records specifying sets of rules that are used in different combinations to translate the inbound message. Individual configuration records may reference different combinations of sets of rules to apply as translation to the inbound message to translate the medical record content of the inbound message from the first medical record content to a standardized format. The standardized format may be provided to the vendor entity indicated by the inbound message.

Referring back to FIG. 1, transmission component 112 may be configured to effectuate transmission of the standardized format to the vendor entity and/or an application associated with the vendor entity indicated within the inbound message. Transmission component 112 may be configured to apply a filter that determines whether to continue transmitting the standardized format to the vendor entity and/or an application associated with the vendor entity. For example, some healthcare and/or vendor entities may only want messages from particular departments to be sent out. Filters may alter the content of the messages, such that only required information may be transmitted (e.g., only required information for a scheduling application, and/or other required information associated with other applications). The filters may filter such information out of the inbound message, such that the vendor entity and/or the application associated with the vendor entity only receive information permitted to be transmitted and/or released by the healthcare entity. The standardized format may be consumed by an application associated with the vendor entity via an application program interface associated with system 100. Some departments at healthcare providers and/or clinics do not want particular medical record content to be transmitted. The filters may be provided by the individual healthcare entities and/or the individual vendor entities. The filters may be configured, added, deleted, customized, and/or modified by users of the individual healthcare entities and/or the individual vendor entities. The filters may be stored within electronic storage 122.

Sometimes messages may be sent from an originating entity (e.g., a healthcare entity) to a receiving entity (e.g., a vendor entity and/or an application associated with the vendor entity) and the originating entity may not expect a response. Other times, the receiving entity (e.g., the vendor entity and/or an application associated with the vendor entity) may respond to the message from the originating entity (e.g., the healthcare entity). System 100 may be configured to receive, from the vendor entity, a vendor message (e.g., a response from the receiving entity for the originating entity). The vendor message may include medical record content in the standardized format. The vendor message may indicate one or more healthcare entities and the vendor entity. Referring back to FIG. 2, system 100 may be configured to receive, from vendor entity 202a, a vendor message indicating one or more healthcare entities 200a, 200b, . . . 200n.

Based upon the stored correspondences, as discussed above, and the indication of the one or more healthcare entities in the vendor message, system 100 may be configured to determine one or more medical record formats to translate the vendor message into. For example, if healthcare entity 200a is associated with the HL7 medical record format, system 100 may be configured to determine that the vendor message may be translated into the HL7 medical record format before transmitting the vendor message to healthcare entity 200a. If healthcare entity 200b is associated with the XML medical record format, system 100 may be configured to determine that the vendor message may be translated into the XML medical record format before transmitting the vendor message to healthcare entity 200b. A single message and/or response may be translated into more than one medical record format based upon the different healthcare entities the message may be transmitted to.

Based on the determination that the medical record content of the vendor message is to be translated into one or more medical record formats, system 100 may be configured to generate one or more outbound messages based upon the one or more medical record formats to translate the vendor message into. Referring to the example above, if a first outbound message is to be transmitted to healthcare entity 200a, system 100 may be configured to translate the vendor message into the HL7 medical record format in a similar manner as described above. If a second outbound message is to be transmitted to healthcare entity 200b, system 100 may be configured to translate the vendor message into the XML medical record format. The translation from the standardized format to the medical record format may include applying a set of rules, similar to the configuration records discussed above, to translate the standardized format to the medical record format by translating the standardized format into a structured object that represents the outgoing medical record format. The structured object may then be converted into a string to be included within a message payload for the healthcare entity.

In some implementations, messages may be sent bi-directionally between healthcare entities and vendor entities and/or applications associated with vendor entities. System 100 may be configured to translate the messages being transmitted to or from the medical record format to or from the standard format in or near real-time. As discussed above, sometimes messages may be transmitted to more than one healthcare entity, individual healthcare entities being associated with the same or different medical record formats. Even if two different healthcare entities are associated with the same or similar medical record format, the individual same or similar medical record formats may differ based upon customizations of the healthcare entity associated with the medical record format. System 100 may be configured to translate messages in or near real-time of transmission regardless of the quirks of individual medical record formats.

System 100 may be configured to effectuate transmission of the individual outbound messages to the individual healthcare entities.

System 100 may be configured to operate in or near real-time with message processing across system 100 averaging less than 400 milliseconds. This allows applications and/or users to use system 100 to power real-time workflows. As such, system 100 may be configured to allow for accelerated translation and normalization.

Referring again to FIG. 1, in some implementations, server(s) 102, client computing platform(s) 104, and/or external resources 120 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 120 may be operatively linked via some other communication media.

A given client computing platform 104 may include one or more processors configured to execute computer program components. The computer program components may be configured to enable a producer and/or user associated with the given client computing platform 104 to interface with system 100 and/or external resources 120, and/or provide other functionality attributed herein to client computing platform(s) 104. By way of non-limiting example, the given client computing platform 104 may include one or more of a desktop computer, a laptop computer, a handheld computer, a NetBook, a Smartphone, a gaming console, and/or other computing platforms.

External resources 120 may include sources of information, hosts and/or providers of virtual environments outside of system 100, external entities participating with system 100, and/or other resources. In some implementations, some or all of the functionality attributed herein to external resources 120 may be provided by resources included in system 100.

Server(s) 102 may include electronic storage 122, one or more processors 124, and/or other components. Server(s) 102 may include communication lines, or ports to enable the exchange of information with a network and/or other computing platforms. Illustration of server(s) 102 in FIG. 1 is not intended to be limiting. Servers(s) 102 may include a plurality of hardware, software, and/or firmware components operating together to provide the functionality attributed herein to server(s) 102. For example, server(s) 102 may be implemented by a cloud of computing platforms operating together as server(s) 102.

Processor(s) 124 may be configured to provide information processing capabilities in server(s) 102. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1 as a single entity, this is for illustrative purposes only. In some implementations, processor(s) 124 may include a plurality of processing units. These processing units may be physically located within the same device, or processor(s) 124 may represent processing functionality of a plurality of devices operating in coordination. The processor(s) 124 may be configured to execute computer readable instruction components 106, 108, 110, 112, and/or other components. The processor(s) 124 may be configured to execute components 106, 108, 110, 112, and/or other components by software; hardware; firmware; some combination of software, hardware, and/or firmware; and/or other mechanisms for configuring processing capabilities on processor(s) 124.

It should be appreciated that although components 106, 108, 110, and 112 are illustrated in FIG. 1 as being co-located within a single processing unit, in implementations in which processor(s) 124 includes multiple processing units, one or more of components 106, 108, 110, and/or 112 may be located remotely from the other components. The description of the functionality provided by the different components 106, 108, 110, and/or 112 described herein is for illustrative purposes, and is not intended to be limiting, as any of components 106, 108, 110, and/or 112 may provide more or less functionality than is described. For example, one or more of components 106, 108, 110, and/or 112 may be eliminated, and some or all of its functionality may be provided by other ones of components 106, 108, 110, and/or 112. As another example, processor(s) 124 may be configured to execute one or more additional components that may perform some or all of the functionality attributed herein to one of components 106, 108, 110, and/or 112.

Figure 4:
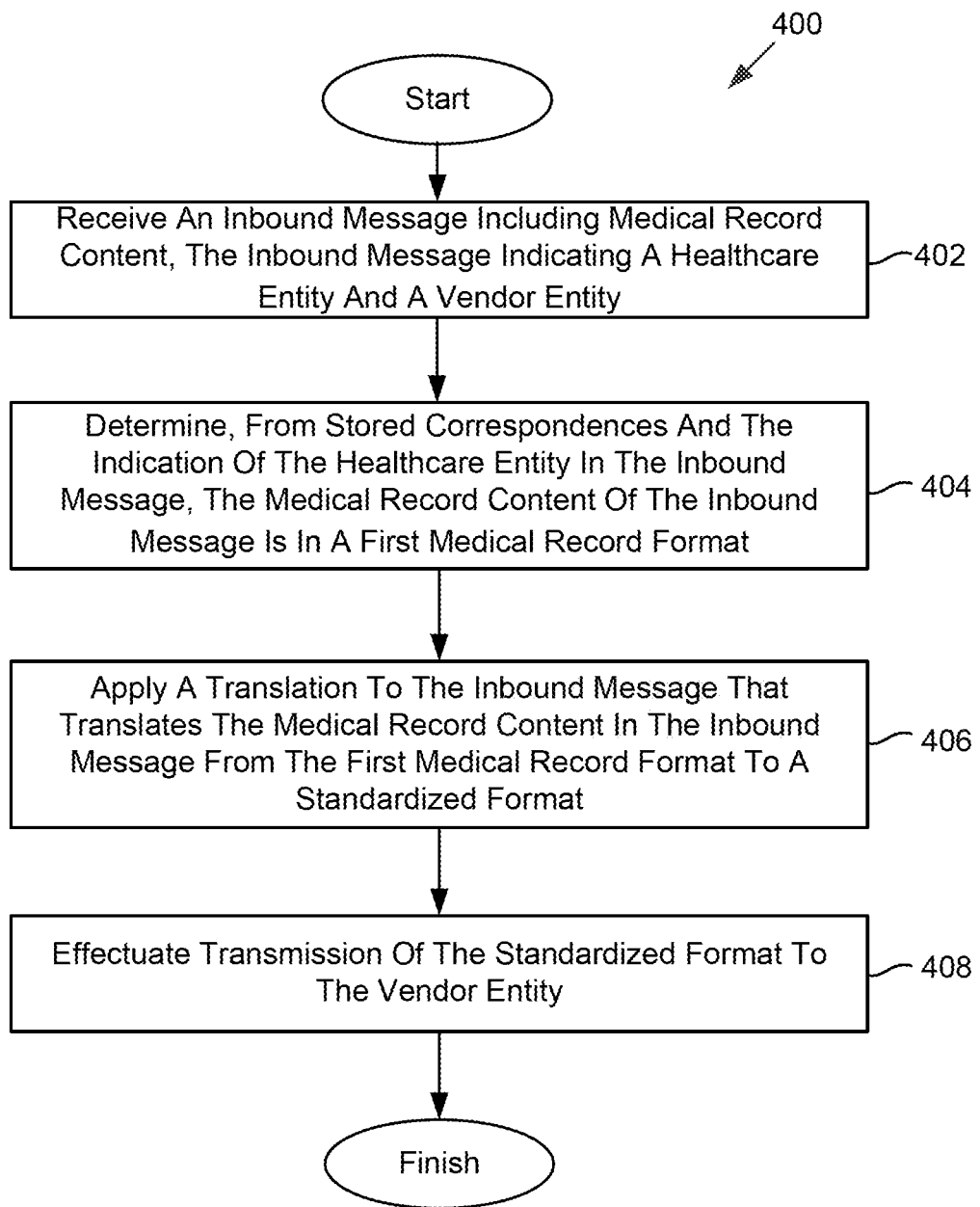
FIG. 4 illustrates a method for translating messages that include medical record content between a healthcare entity and a vendor entity, in accordance with one or more implementations.
Figure 5:
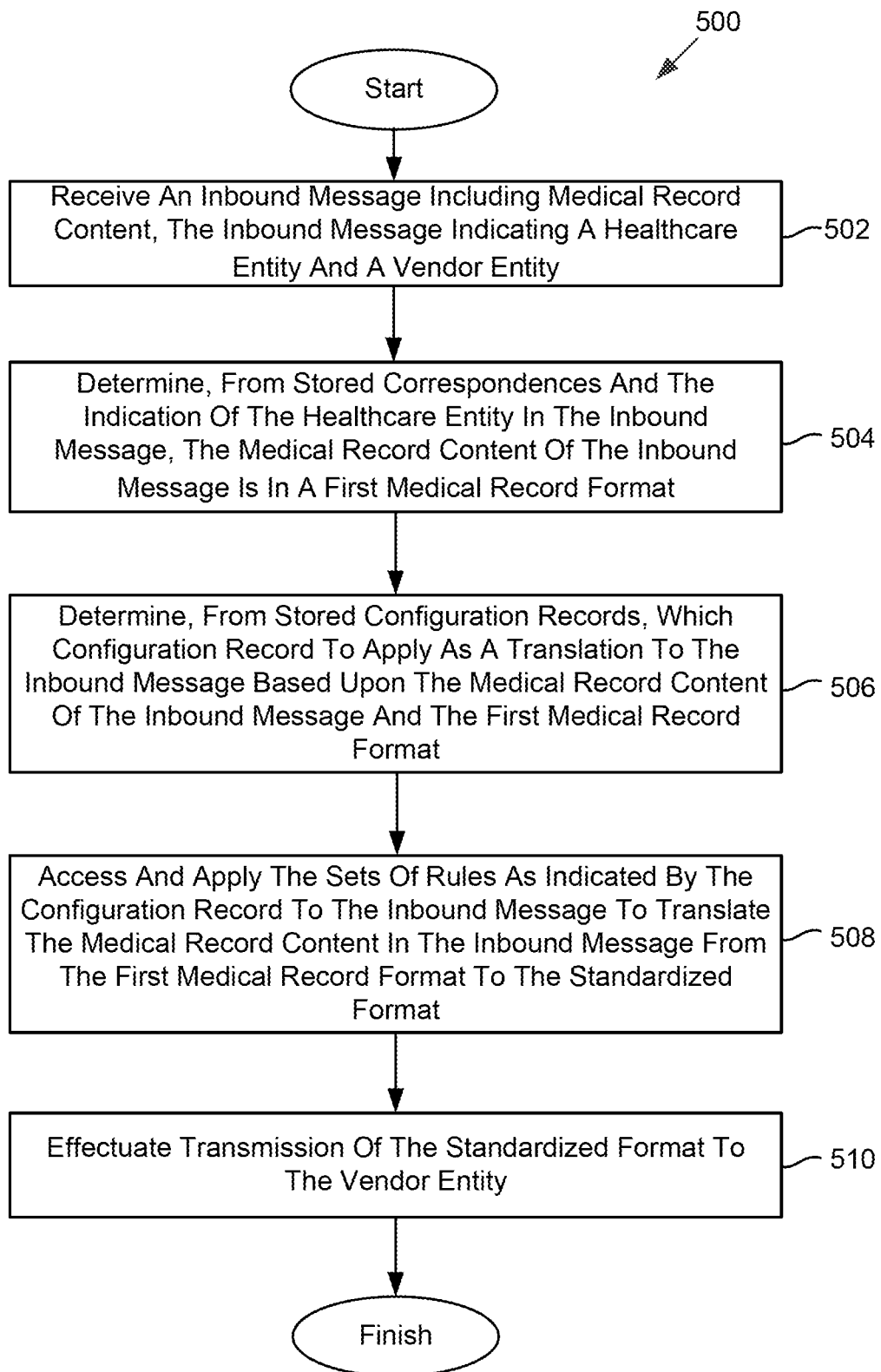
FIG. 5 illustrates a method for translating messages that include medical record content between a healthcare entity and a vendor entity, in accordance with one or more implementations.

FIGS. 4 and 5 illustrate methods 400 and 500, respectively, for translating messages that include medical record content between a healthcare entity and a vendor entity, in accordance with one or more implementations. The operations of methods 400 and 500 presented below are intended to be illustrative. In some implementations, methods 400 and 500 may be accomplished with one or more additional operations not described, and/or without one or more of the operations discussed. Additionally, the order in which the operations of methods 400 and 500 are illustrated in FIGS. 4 and 5 described below is not intended to be limiting.

In some implementations, methods 400 and/or 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of methods 400 and/or 500 in response to instructions stored electronically on an electronic storage medium. The one or more processing devices may include one or more devices configured through hardware, firmware, and/or software to be specifically designed for execution of one or more of the operations of methods 400 and/or 500.

Referring to FIG. 4, at an operation 402, an inbound message including medical record content may be received. The inbound message may indicate the healthcare entity and the vendor entity. Operation 402 may be performed by a receiving component that is the same as or similar to receiving component 106, in accordance with one or more implementations.

At an operation 404, the medical record content of the inbound message may be determined to be in a first medical record format based upon stored correspondences between medical record formats and healthcare entities and the indication of the healthcare entity in the inbound message. Operation 404 may be performed by a determination component that is the same as or similar to determination component 108, in accordance with one or more implementations.

At an operation 406, a translation may be applied to the inbound message based upon the determination that the medical record content of the inbound message is in the first medical record format. The translation may translate the medical record content in the inbound message from the first medical record format to a standardized format. Operation 406 may be performed by a translation component that is the same as or similar to translation component 110, in accordance with one or more implementations.

At an operation 408, the standardized format may be transmitted to the vendor entity. Operation 408 may be performed by a transmission component that is the same as or similar to transmission component 112, in accordance with one or more implementations.

Referring to FIG. 5, at an operation 502, an inbound message including medical record content may be received. The inbound message may indicate the healthcare entity and the vendor entity. Operation 502 may be performed by a receiving component that is the same as or similar to receiving component 106, in accordance with one or more implementations.

At an operation 504, the medical record content of the inbound message may be determined to be in a first medical record format based upon stored correspondences between medical record formats and healthcare entities and the indication of the healthcare entity in the inbound message. Operation 504 may be performed by a determination component that is the same as or similar to determination component 108, in accordance with one or more implementations.

At an operation 506, which configuration record to apply as a translation to the inbound message may be determined from stored configuration records based upon the medical record content of the inbound message and the first medical record format. Operation 506 may be performed by a translation component that is the same as or similar to translation component 110, in accordance with one or more implementations.

At an operation 508, the sets of rules may be accessed and applied as indicated by the configuration record to the inbound message to translate the medical record content in the inbound message from the first medical record format to the standardized format. Operation 508 may be performed by a translation component that is the same as or similar to translation component 110, in accordance with one or more implementations.

At an operation 510, the standardized format may be transmitted to the vendor entity. Operation 510 may be performed by a transmission component that is the same as or similar to transmission component 112, in accordance with one or more implementations.

Although the system(s) and/or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A system configured to convert messages communicated between a healthcare entity and a vendor entity, the messages including medical record content, the system comprising:
   physical non-transitory electronic storage storing:
      correspondence information, wherein the correspondence information specifies correspondences between medical record formats of electronic medical records and healthcare entities, the medical record formats being customized by individual healthcare entities, the customizations including locations of medical record content within the electronic medical records, such that an individual medical record format corresponds to an individual healthcare entity; and
      configuration record information, wherein the configuration record information includes configuration records specifying individual combinations of rules to convert messages between the medical record formats and a standardized medical record format, an individual configuration record specifying an individual combination of rules to convert messages between the individual medical record format and the standardized medical record format; and
   one or more physical computer processors configured by computer readable instructions to:
      receive an inbound message including particular medical record content, the inbound message indicating the individual healthcare entity and a vendor entity;
      determine, from the correspondence information and the configuration record information, which configuration record to use to convert the inbound message to the standardized medical record format, wherein determination of the individual configuration record is based upon the particular medical record content of the inbound message and the indication of the first healthcare entity;
      responsive to determination of the individual configuration record, apply the individual combination of rules to the inbound message to convert the particular medical record content in the inbound message from the individual medical record format to the standardized medical record format; and
      effectuate transmission of the particular medical record content in the inbound message in the standardized medical record format to the vendor entity.

2. The system of claim 1, wherein the individual medical record format is similar to at least one other medical record format.

3. The system of claim 1, wherein the individual medical record format and the other individual medical record formats differ based upon customizations by the individual healthcare entities.

4. The system of claim 3, wherein the individual combination of rules in the sets of rules specify the differences between the individual medical record format and the other individual medical record formats based upon the customizations.

5. The system of claim 1, wherein a first rule in the individual combination of rules includes parsing the particular medical record content in the inbound message into structured objects including data fields.

6. The system of claim 5, wherein a second rule in the individual combination of rules includes converting the data fields from the structured objects into standardized format fields of the standardized format.

7. The system of claim 1, wherein one or more configuration records specify sets of rules that reference nested configuration records.

8. The system of claim 7, wherein the nested configuration records specify combinations of sets of rules that are common between the one or more configuration records that reference the nested configuration records.

9. The system of claim 1, wherein the particular medical record content includes an electronic health record.

10. The system of claim 1, wherein the individual medical record formats follow one or more standards of communication.

11. A method to convert messages communicated between a healthcare entity and a vendor entity, the messages including medical record content, the method being implemented in a computer system comprising one or more physical computer processors and non-transitory electronic storage, the method comprising:

obtaining, by the one or more physical computer processors, correspondence information, the correspondence information specifying correspondences between medical record formats of electronic medical records and healthcare entities, the medical record formats being customized by individual healthcare entities, the customizations including locations of medical record content within the electronic medical records, such that an individual medical record format corresponds to an individual healthcare entity;

obtaining, by the one or more physical computer processors, configuration record information, the configuration record information including configuration records specifying individual combinations of rules to convert messages between the medical record formats and a standardized medical record format, an individual configuration record specifying an individual combination of rules to convert messages between the individual medical record format and the standardized medical record format;

receiving, by the one or more physical computer processors, an inbound message including particular medical record content, the inbound message indicating the individual healthcare entity and a vendor entity;

determining, by the one or more physical computer processors from the correspondence information and the configuration record information, which configuration record to use to convert the inbound message to the standardized medical record format, wherein determination of the individual configuration record is based upon the particular medical record content of the inbound message and the indication of the first healthcare entity;

responsive to determination of the individual configuration record, applying the individual combination of rules to the inbound message to convert the particular medical record content in the inbound message from the individual medical record format to the standardized medical record format; and effectuating, by the one or more physical computer processors, transmission of the particular medical record content in the inbound message in the standardized medical record format to the vendor entity.

12. The method of claim 11, wherein the individual medical record format is similar to at least one other medical record format.

13. The method of claim 11, wherein the individual medical record format and the other individual medical record formats differ based upon customizations by the individual healthcare entities.

14. The method of claim 13, wherein the individual combination of rules in the sets of rules specify the differences between the individual medical record format and the other individual medical record formats based upon the customizations.

15. The method of claim 11, wherein a first rule in the individual combination of rules includes parsing the medical record content in the inbound message into structured objects including data fields.

16. The method of claim 15, wherein a second rule in the individual combination of rules includes converting the data fields from the structured objects into standardized format fields of the standardized format.

17. The method of claim 11, wherein one or more configuration records specify sets of rules that reference nested configuration records.

18. The method of claim 17, wherein the nested configuration records specify combinations of sets of rules that are common between the one or more configuration records that reference the nested configuration records.

19. The method of claim 11, wherein the particular medical record content includes an electronic health record.

20. The method of claim 11, wherein the individual medical record formats follow one or more standards of communication.

* * * * *